United States Patent [19]

Chien

[11] Patent Number: 4,849,988
[45] Date of Patent: Jul. 18, 1989

[54] APPARATUS AND METHOD FOR MEASURING THE QUALITY OF STEAM

[75] Inventor: Sze-Foo Chien, Houston, Tex.

[73] Assignee: Texaco Inc., White Plains, N.Y.

[21] Appl. No.: 158,425

[22] Filed: Feb. 19, 1988

[51] Int. Cl.[4] .......................... G01N 9/00; G01N 25/60
[52] U.S. Cl. ........................................... 374/42; 73/29;
364/557; 364/558
[58] Field of Search ............... 364/558; 374/42; 73/29

[56] References Cited

U.S. PATENT DOCUMENTS

| | | | |
|---|---|---|---|
| 2,718,619 | 9/1955 | Whittier | 324/61 QL |
| 3,100,395 | 8/1963 | Morley | 374/42 |
| 3,776,034 | 12/1973 | Kolb | 364/558 X |
| 4,149,403 | 4/1979 | Muldary et al. | 374/42 X |
| 4,681,466 | 7/1987 | Chien et al. | 374/42 |
| 4,753,106 | 6/1988 | Brennet et al. | 374/42 X |
| 4,769,593 | 9/1988 | Reed et al. | 73/29 X |

*Primary Examiner*—Daniel M. Yasich
*Attorney, Agent, or Firm*—Robert A. Kulason; James J. O'Loughlin; Ronald G. Gillespie

[57] ABSTRACT

Steam quality measuring and monitoring apparatus and methods which measures the quality of steam flowing in a steam pipe includes a test cell connected in line with the steam pipe so that the steam flows through the test cell. The capacitance, the dielectric constant, the temperature and the density of the steam flowing through the test cell are measured and monitored and the quality of the steam is derived in accordance with the steam density and temperature.

6 Claims, 1 Drawing Sheet

APPARATUS AND METHOD FOR MEASURING THE QUALITY OF STEAM

BACKGROUND OF THE INVENTION

1. Field of the Invention

The present invention relates to measure and to monitor steam quality in general and, more particularly to measure and to monitor the quality to steam flowing in a steam pipe.

SUMMARY OF THE INVENTION

Steam quality measuring and apparatus and methods, which determine the quality of steam flowing in a steam pipe, include a test cell connected in line with the steam pipe so that the steam flows through the test cell. The density and the temperature of the steam flowing through the test cell is measured and monitored and the quality of the steam is derived in accordance with the steam density and the steam temperature.

The objects and advantages of the invention will be described more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE DRAWINGS

With reference to FIG. 1, a pipe 3 carry steam has interconnected with it a test cell 8, which is basically made of non-conductive material. The flanges of test cell 8 and of steam pipes 3 are bolted together with bolts not shown.

Figure 1:
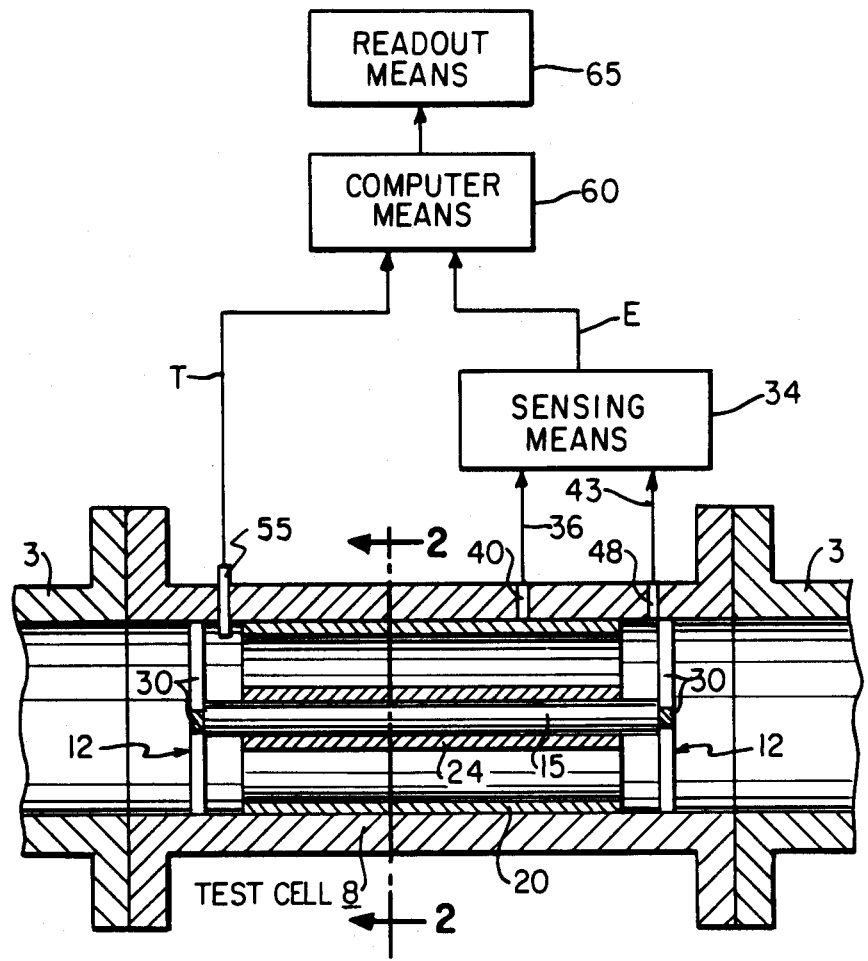
FIG. 1 is a partial simplified block diagram and partial assembly drawing of a steam quality constructed in accordance with the present invention.
Figure 2:
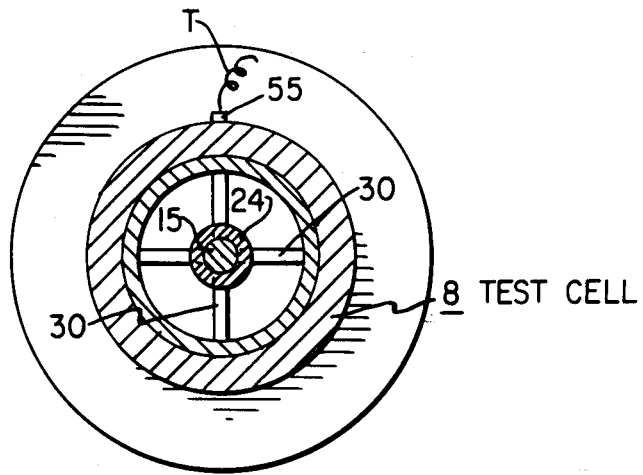
FIG. 2 is a cross-sectional view of the test cell shown in FIG. 1.

Test cell 8 includes stanchions 12 which fit within the interior channel of test cell 8 and are used to support a support element 15 between them. Again, stanchions and support element 15 are also made of non-conductive material. A metallic cylindrical conductor 20 is affixed to the interior surface of test cell 8, while another metallic cylindrical conductor 24 is affixed to support element 15. Thus conductors 20 and 24 form a cylindricalcapacitor. With reference also to FIG. 2, stanchion 12 can be seen as not to be a solid element, but rather one that has a rim with radial support arms or spokes 30 which allows stanchions 12 to support element 15 while at the same time permitting fluid flow through stanchions 12 and the space between the two cylindrical conductors.

A temperature sensor 55 is connected through test cell 8 into the stream flow and senses the temperature of the steam to provide a signal T corresponding to the sensed temperature.

Conductor 20 is electrically connected to a capacitance sensing means 34 by an electrical wire 36 which passes through a sealed port 40 in cell 8.

Similarly, conductor 24 is electrically connected to the capacitance sensing means 34 by an electrical wire 43 which passes through a sealed port 48 in test cell 8. The capacitance sensing means 34 is to provide necessary electrical signals needed for the measurement of the capacitance of the steam flowing through the space of the capacitor; and to convert the sensed capacitance into a signal E corresponding to the dielectric constant of the flowing steam. The capacitance and the dielectric constant are related by Equation 1.

$$1. \quad C = bE$$

where b is a constant, its magnitude depends on the design of the cylindrical capacitor, such as the diameters, the diameter ratio and the length of the cylindrical conductors.

Signals E and T are provided to the computer means 60 which determines the steam quality and provides an output corresponding to the steam quality to readout means 65. The computer means 60 first determines the steam density P in accordance with empirical equation such as equation 2 and then determines the steam quality in accordance with equation 4.

$$2. \quad E = 1 + (a_1/T^*)P^* + (a_2/T^* + a_3 + a_4T^*)P^{*2} + (a_5/T^* + a_6T^* + a_7T^{*2})P^{*3} + (a_8/T^{*2} + a_9T^* + a_{10})P^{*4}$$

where E is the dielectric constant, T is temperature in Kelvin, and T* equals T/298.15 and P is density in Kg/m3, while P* equals P/1000. The values of $a_1$ through $a_{10}$ are shown in the following Table I:

TABLE I

| | |
|---|---|
| $a_1 = 7.62571 \times 10^0$ | $a_6 = 4.17909 \times 10^1$ |
| $a_2 = 2.44003 \times 10^2$ | $a_7 = -1.02099 \times 10^1$ |
| $a_3 = -1.40569 \times 10^2$ | $a_8 = -4.52059 \times 10^1$ |
| $a_4 = 2.77841 \times 10^1$ | $a_9 = 9.46395 \times 10^1$ |
| $a_5 = -9.62805 \times 10^1$ | $a_{10} = 3.58655 \times 10^1$ |

The steam density P is rotated to steam quality X by the following equation:

$$3. \quad P = 1/[V_f + x(V_g - V_f)]$$

where $V_f$ is the specific volume of saturated liquid, $V_g$ is the specific volume of saturated vapor, and X is the steam quality. For a given temperature, $V_f$ and $V_g$ are constants, so that density is directly related to steam quality. Specific volumes for steam are obtainable either from steam tables or pre-encoded computer disks of steam properties.

Equation 3 may be rewritten as $$4. \quad x = (1/P - V_f)/(V_g - V_f)$$

It should be noted that although the present invention has been shown as using a temperature sensor 55 to provide a signal T, the present invention may be also practiced using a pressure sensor to sense the pressure of the steam in pipe 3 and provides a signal corresponding to the steam pressure.

Computer means 60 in operation with sensed signal E, which is varied proportionately to the dielectric constant of the steam, and sensed temperature signal T, which is varied proportional to the steam temperature, to determine the steam density. Computer means 60 varies the density P and hence the density P* in sequential steps until equation 2 is substantially balanced. At that time P is then used with equation 4, along with stored values $V_f$ and $V_g$, to determine steam quality x.

What is claimed is:

1. Steam quality apparatus which measures and monitors the quality of steam flowing in a steam pipe comprising:
   a test cell connected in line with the steam pipe in a manner so that the steam flows through the test cell,
   capacitance sensing means contained within the test cell for providing a capacitance output corresponding to the capacitance of the steam,
   temperature sensing means for sensing the temperature of the steam and providing a temperature signal representative thereof,
   density determining means connected to the capacitance sensing means and to the temperature sensing means for monitoring the density of the steam flowing through the test cell, and
   means connected to the density determining means and to the temperature sensing means for deriving the steam quality in accordance with the steam density and the temperature signal and providing a steam quality output related thereto; and
   in which the density determining means includes:
   dielectric constant determining means connected to capacitance sensing means for utilizing the capacitance output to determine the dielectric constant of the flowing steam and providing a signal E corresponding thereto, and
   computer means connected to the dielectric electric constant determining means and to the temperature sensing means for determining the steam density in accordance with the following equation:

$$E = 1 + (a_1/T^*)P^* + (a_2/T^* + a_3a_4T^*) P^{*2} +$$
$$(a_5/T^* + a_6T^* + a_7T^{*2}) P^{*3} + (a_8/T^{*2} + a_9T^* + a_{10}) P^{*4}$$

where E is the dielectric constant, T is temperature in degree Kelvin, T* equals T/298.15 and P is density in Kg/m$^3$ while P* equals P/1000, and $a_1$ through $a_{10}$ are constants.

2. Apparatus as described in claim 1 in which the test cell includes:
   pipe means made of non-conductive material for connecting in line with the steam pipe,
   first conductive material mounted on the inner surface of the pipe means,
   a non-conductive member,
   means mounted inside of the pipe means for supporting the non-conductive member along a central longitudinal axis of the test cell,
   second conductive material mounted on the non-conductive member and spatially arranged with the first conductive material so as to form a cylindrical capacitor, and
   in which the density determining means is electrically connected to both conductive materials.

3. An apparatus as described in claim 2 in which the steam quality means determines the steam quality from sensed signal P and in accordance with the following equation:

$$x = (1/P - V_f)/(V_g - V_f)$$

where x is steam quality, $V_f$ is the specific volume of saturated liquid and $V_g$ is the specific volume of saturated vapor for the steam temperature T.

4. A method of measuring and monitoring the quality of steam flowing in a steam pipe comprising the steps of:
   connecting a test cell in line with the steam pipe in a manner so that the steam flows through the test cell,
   sensing the capacitance of the steam in the test cell,
   providing a capacitance output corresponding to the sensed capacitance,
   sensing the temperature of the steam,
   providing a temperature signal representative of the sensed temperature,
   utilizing the capacitance output and the temperature signal to determine the density of the steam,
   providing a steam density signal related to the determined density, and
   deriving a quality of the steam in accordance with the steam density and the temperature signals; and
   in which the density determining step includes:
   utilizing the capacitance output to determine the dielectric constant in accordance with the following equation $$C = bE$$

where E is the dielectric constant and b is a constant depending on the design of the cylindrical capacitor,
   providing a dielectric constant signal representative of the determined dielectric constant,
   determining the steam density with a computer and in accordance with the following equation:

$$E = 1 + (a_1/T^*)P^* + (a_2/T^* + a_3a_4T^*) P^{*2} +$$
$$(a_5/T^* + a_6T^* + a_7T^{*2}) P^{*3} + (a_8/T^{*2} + a_9T^* + a_{10}) P^{*4}$$

where E is the dielectric constant, T is temperature in degree Kelvin, and T* equals T/298.15 and P is density in Kg/m$^3$, while P* equals P/1000, and $a_1$ through $a_{10}$ are constants, and
   providing a density signal P corresponding to the determined density.

5. A method as described in claim 4 in which the connecting the test cell step includes:
   connecting a pipe made of non-conductive material, in line with the steam pipe,
   mounting first conductive material on the inner surface of the non-conductive pipe,
   mounting a non-conductive member, mounted inside of the test cell along a central longitudinal axis of the test cell in a manner so as to permit steam flow through the test cell,
   mounting second conductive material on the non-conductive member in a manner so as to form a capacitor in cooperation with the first conductive material, and
   in which the density determining step includes using electrical connections to both conductive materials.

6. A method as described in claim 5 in which the steam quality step includes determining the steam quality with the computer in accordance with the density signal P and the following equation:

$$3. \; x = (1/P - V_f)/(V_g - V_f)$$

where x is steam quality, $V_f$ is the specific volume of saturated liquid and $V_g$ is the specific volume of saturated vapor at the sensed steam temperature.

* * * * *